(12) United States Patent
Cai et al.

(10) Patent No.: US 11,179,392 B2
(45) Date of Patent: Nov. 23, 2021

(54) SOLID PHARMACEUTICAL FORMULATION OF PARP INHIBITORS AND USE THEREOF

(71) Applicant: IMPACT THERAPEUTICS, INC., Shanghai (CN)

(72) Inventors: Suixiong Cai, Shanghai (CN); Yushen Guo, Shanghai (CN)

(73) Assignee: IMPACT THERAPEUTICS, INC., Shanghai (CN)

( * ) Notice: Subject to any disclaimer, the term of this patent is extended or adjusted under 35 U.S.C. 154(b) by 0 days.

(21) Appl. No.: 15/562,730

(22) PCT Filed: Apr. 1, 2016

(86) PCT No.: PCT/CN2016/078262
§ 371 (c)(1),
(2) Date: Sep. 28, 2017

(87) PCT Pub. No.: WO2016/155655
PCT Pub. Date: Oct. 6, 2016

(65) Prior Publication Data
US 2018/0071290 A1 Mar. 15, 2018

(30) Foreign Application Priority Data
Apr. 3, 2015 (CN) .......................... 201510157453.X (51) Int. Cl.
| A61K 31/497 | (2006.01) |
| A61K 31/517 | (2006.01) |
| A61K 47/38  | (2006.01) |
| A61K 9/14   | (2006.01) |
| A61K 47/32  | (2006.01) |
| A61K 9/16   | (2006.01) |
| A61K 45/06  | (2006.01) |

(52) U.S. Cl.
CPC .............. *A61K 31/517* (2013.01); *A61K 9/14* (2013.01); *A61K 9/1641* (2013.01); *A61K 9/1652* (2013.01); *A61K 45/06* (2013.01); *A61K 47/32* (2013.01); *A61K 47/38* (2013.01); *A61K 2300/00* (2013.01)

(58) Field of Classification Search
CPC .. A61K 31/517; A61K 9/1641; A61K 9/1652; A61K 45/06
See application file for complete search history.

(56) References Cited

U.S. PATENT DOCUMENTS

| 2008/0274192 | A1* | 11/2008 | Friesen ................. A61K 9/1652 |
|              |     |         |                           424/488 |
| 2014/0275711 | A1  | 9/2014  | Cai et al. |
| 2015/0011525 | A1* | 1/2015  | Bi ......................... A61K 9/146 |
|              |     |         |                           514/210.02 |

FOREIGN PATENT DOCUMENTS

| CN | 101668527 A    | 3/2010  |
| CN | 104230827 A    | 12/2014 |
| JP | 2012-505158 A  | 10/2009 |
| WO | WO 2008/103914 A1 | 8/2008 |
| WO | WO 2010/041051 A1 | 4/2010 |
| WO | WO 2010/078897 A1 | 7/2010 |
| WO | WO 2012/130166 A1 | 10/2012 |

OTHER PUBLICATIONS

Leuner, C., et al., "Improving drug solubility for oral delivery using solid dispersions," *European Journal of Pharmaceutics and Biopharmaceutics* 50:47-60, Elsevier Science B.V., Netherlands (2000).
International Search Report and Written Opinion for International Application No. PCT/CN2016/078262, Chinese Patent Office, China, dated Jul. 4, 2016, 7 pages.
Supplementary European Search Report for EP Application No. EP 16 77 1410, Munich, Germany, dated Oct. 8, 2018, 9 pages.
Khan, G.M., et al., "Preparation, Characterization, and Dissolution Studies of Ibuprofen Solid Dispersions Using Polyethylene Glycol (PEG), Talc, and PEG-Talc as Dispersion Carriers," *Drug Development and Industrial Pharmacy* 24(5):455-462 (1998) (Abstract Only).
Sharma, M., et. al., "Formulation and Evaluation of Solid Dispersion of Atorvastatin Calcium," *Journal of Pharmaceutical and Scientific Innovation* 2(4):73-81 (2013).
Van Duong, T., et al., "The role of the carrier in the formulation of pharmaceutical solid dispersions. Part II: amorphous carriers," *Expert Opinion on Drug Delivery* 13(12):1681-1694 (2016).
Stroh, M., et al., "Clinical Pharmacokinetics and Pharmacodynamics of Atezolizumab in Metastatic Urothelial Carcinoma," *Clinical Pharmacology & Therapeutics* 102(2): 305-312 (2017).
Cao, J., et al., "Pooled analysis of phase I dose-escalation and dose cohort expansion studies of IMP4297, a novel PARP inhibitor, in Chinese and Australian patients with advanced solid tumors" *2019 ASCO Annual meeting, Abstract ID: 3059.*

(Continued)

*Primary Examiner* — Shobha Kantamneni
(74) *Attorney, Agent, or Firm* — Sterne, Kessler, Goldstein & Fox P.L.L.C.

(57) ABSTRACT

The present invention provides a solid pharmaceutical formulation of PARP inhibitors and its use thereof, and more specifically a solid dispersion powder including 5-fluoro-1-(4-fluoro-3-(4-(pyrimidin-2-yl)piperazine-1-carbonyl)benzyl)quinazoline-2,4(1H,3H)-dione and polymers, wherein the content of polymers is from about 50 wt % to about 80 wt %, and wherein less than 10 wt % of 5-fluoro-1-(4-fluoro-3-(4-(pyrimidin-2-yl)piperazine-1-carbonyl)benzyl) quinazoline-2,4(1H,3H)-dione is in crystalline form. The present invention also provides a method for preparing the solid dispersion powder, a pharmaceutical composition including the solid dispersion powder and the use of the pharmaceutical composition for treating diseases caused by PARP activity abnormalities.

7 Claims, 2 Drawing Sheets

(56) References Cited

OTHER PUBLICATIONS

United States Pharmacopeia—National Formulary, "Hypromellose Phthalate," Official Monographs NF35: 7706-7707, United States Pharmacopeia Convention, United States (2017).
United States Pharmacopeia—National Formulary, "Hypromellose Acetate Succinate," Official Monographs NF35: 7704-7706, United States Pharmacopeia Convention, United States (2017).
Shin-Etsu Chemical Co. Ltd., "Hypromellose Phthalate: Enteric Coating Material," Cellulose & Pharmaceutical Excipients Department; 10 pages, Japan (2002).
Parchem, "Hydroxypropyl Methylcellulose Phthalate, USP 55 HP," CAS No. 9050-31-1, Obtained from the world wide web at parchem.com/chemical-supplier-distributor/Hydroxypropyl-Methylcellulose-Phthalate-USP-55-HP-000677.aspx, on Mar. 2, 2021, 1 page, United States.
Chinese Pharmacopeia, "Hypromellose Acetate Succinate," 2 pages, China Food and Drug Administration, China (2015).
Chinese Pharmacopeia, "Hypromellose Phthalate," 1 page, China Food and Drug Administration, China (2015).

\* cited by examiner

SOLID PHARMACEUTICAL FORMULATION OF PARP INHIBITORS AND USE THEREOF

BACKGROUND OF THE INVENTION

Field of the Invention

This invention generally relates to solid pharmaceutical formulations, and more specifically to pharmaceutical formulations of amorphous solid dispersion comprising 5-fluoro-1-(4-fluoro-3-(4-(pyrimidin-2-yl)piperazine-1-carbonyl)benzyl)quinazoline-2,4(1H,3H)-dione.

Related Art

Poly (ADP-ribose) polymerase (PARP) catalyzes the addition of poly (ADP-ribose) to the target protein using NAD+ that is an important process in DNA repair. This is an essential process for maintaining DNA and chromosome integrity and stability, and for ensuring the survival of mammalian cells. PARP-1 catalyzes the majority of the intracellular ADP-ribose polymerization reactions. Phase II clinical trial data have shown that PARP-1 inhibitor Olaparib (AZD2281) is effective for the treatment of BRCA mutated breast cancer. Olaparib (Lynparza) was approved by EMEA and FDA for the treatment of BRCA mutated ovarian cancer in December 2014. The applications of PARP-1 inhibitors for the treatment of cancer are mainly based on two mechanisms. First, for cancer cells with DNA repair deficiency, such as BRCA1 or BRCA2 deficient triple-negative breast cancer cells and the like, PARP-1 inhibitors can directly kill the cancer cells through the mechanism of synthetic lethality and function as anticancer drugs independently. According to statistics, about 10~15% of breast cancer pateints have family history of genetic factors, in which the BRCA1 or BRCA2 gene mutations account for 15~20% of all hereditary breast cancers. Second, because of the rapid growth of cancer cells, DNA replication is much higher in cancer cells than in normal cells. Drugs that cause DNA damage will induce cancer cell death selectively. However, due to the presence of DNA repair enzymes such as PARP-1, the therapeutic effects of these drugs can not be fully materialized. By inhibiting the DNA repair mechanism, PARP-1 inhibitors in combination with commonly used DNA-damaging chemotherapeutic anti-cancer drugs, such as temozolomide, can achieve synergy effects and greatly enhance the anticancer effects of DNA-damaging anticancer drugs. Furthermore, PARP-1 inhibitors may also be used to treat diseases due to excessive cell death, including central nervous system diseases such as stroke and neurodegenerative diseases (Akinori Iwashita et al., 2004, J. Pharmacol. Exp. Thera. 310: 425).

WO2012130166A1 disclosed the preparation of 1-(arylmethyl)quinazoline-2,4(1H,3H)-diones as PARP inhibitors, wherein some compounds have very poor water solubility, including 5-fluoro-1-(4-fluoro-3-(4-(pyrimidin-2-yl)piperazine-1-carbonyl)benzyl)quinazoline-2,4(1H,3H)-dione.

SUMMARY OF THE INVENTION

The invention has discovered that the amorphous solid dispersions of 5-fluoro-1-(4-fluoro-3-(4-(pyrimidin-2-yl)piperazine-1-carbonyl)benzyl)quinazoline-2,4(1H,3H)-dione can increase the dissolution rate and dissolubility of the compound, so as to improve its bioavailability, as compared to the crystalline forms. Therefore the amorphous solid dispersions of 5-fluoro-1-(4-fluoro-3-(4-(pyrimidin-2-yl)piperazine-1-carbonyl)benzyl)quinazoline-2,4(1H,3H)-dione can be used as anti-cancer drugs for the treatment of cancer.

Therefore, in one aspect, the invention is characterized in the preparation of the amorphous solid dispersions of 5-fluoro-1-(4-fluoro-3-(4-(pyrimidin-2-yl)piperazine-1-carbonyl)benzyl)quinazoline-2,4(1H,3H)-dione. The invention includes a large number of possible formulations, all of which comprise amorphous solid dispersions of 5-fluoro-1-(4-fluoro-3-(4-(pyrimidin-2-yl)piperazine-1-carbonyl)benzyl)quinazoline-2,4(1H,3H)-dione.

In one aspect, the invention is characterized in pharmaceutical compositions including 5-fluoro-1-(4-fluoro-3-(4-(pyrimidin-2-yl)piperazine-1-carbonyl)benzyl)quinazoline-2,4(1H,3H)-dione and a second component. The second component can be selected from multiple components, such as polymers, surfactants, or inert and pharmaceutically acceptable matters. In some preferred embodiments, the composition includes amorphous solid dispersions, mixtures, and liquid dispersions. In some embodiments, the composition is in the form of solid, such as granules, tablets or capsules.

In some embodiments, the amorphous solid dispersion contains crystalline 5-fluoro-1-(4-fluoro-3-(4-(pyrimidin-2-yl)piperazine-1-carbonyl)benzyl)quinazoline-2,4(1H,3H)-dione in an amount of less than about 10%, such as less than about 5% or less than about 1%. For example, in some embodiments, there is nearly no crystalline 5-fluoro-1-(4-fluoro-3-(4-(pyrimidin-2-yl)piperazine-1-carbonyl)benzyl)quinazoline-2,4(1H,3H)-dione within the amorphous solid dispersion.

In some embodiments, the amorphous solid dispersion of 5-fluoro-1-(4-fluoro-3-(4-(pyrimidin-2-yl)piperazine-1-carbonyl)benzyl)quinazoline-2,4(1H,3H)-dione includes enough polymers so that after administration of the solid dispersion, the level of 5-fluoro-1-(4-fluoro-3-(4-(pyrimidin-2-yl)piperazine-1-carbonyl)benzyl)quinazoline-2,4(1H,3H)-dione in the blood of animals such as mice is higher than that in the case of administrating non-amorphous such as crystalline 5-fluoro-1-(4-fluoro-3-(4-(pyrimidin-2-yl)piperazine-1-carbonyl)benzyl)quinazoline-2,4(1H,3H)-dione, for example at least about 100% higher, at least about 200% higher, at least about 400% higher, at least about 600% higher, or at least about 800% higher than the level of 5-fluoro-1-(4-fluoro-3-(4-(pyrimidin-2-yl)piperazine-1-carbonyl)benzyl)quinazoline-2,4(1H,3H)-dione in the case of administrating crystalline one.

In some embodiments, amorphous solid dispersions include cellulose polymers, such as hydroxy propyl cellulose (HPC) polymers, acrylic resin (Eudragit) polymers, hydroxypropyl methylcellulose phthalate (HPMCP, also known as phthalic acid hydroxypropyl methyl cellulose (HP-50, HP-55)) polymers, or hydroxypropyl methylcellulose acetate succinate (HPMCAS) polymers. The content of the polymer within the solid dispersion is about 40% to 80% by weight, such as about 50% by weight, about 60% by weight, about 70% by weight or about 75% by weight, or in the range defined by any two endpoints. In some embodiments, the content of 5-fluoro-1-(4-fluoro-3-(4-(pyrimidin-2-yl)piperazine-1-carbonyl)benzyl)quinazoline-2,4(1H,3H)-dione within the amorphous solid dispersion is about 10% to 40% by weight, such as about 15% by weight, about 20% by weight, about 25% by weight or about 30% by weight, or in the range defined by any two endpoints. In some embodiments, the content of 5-fluoro-1-(4-fluoro-3-

(4-(pyrimidin-2-yl)piperazine-1-carbonyl)benzyl)quinazoline-2,4(1H,3H)-dione within the solid dispersion is more than about 25%.

In some embodiments, the solid dispersions include surfactants, such as Poloxamer 188 or Tween 80. The content of the surfactant in the solid dispersions depends on many factors, such as chemical properties of the surfactant. In some embodiments, the content of the surfactant is about 1% to 10%, such as about 2% to 10%, preferably about 5%.

The amorphous solid dispersion generally shows glass-transition temperature (Tg), and the dispersion changes from vitreous solid into rubber composite at the temperature. In general, the higher the glass transition temperature is, the greater the physical stability of the dispersion is. The exist of Tg commonly shows at least most of the composites (such as dispersions) is in amorphous state. Tg of the solid dispersion suitable for drug application is ordinarily at least about 50° C. In some embodiments, Tg of the solid dispersion in this invention is at least about 70° C., such as at least about 80° C., 90° C., and 100° C. Unless otherwise stated, the glass-transition temperature in this invention is measured by the differential thermal analysis method under dry conditions.

In another aspect, the invention is characterized in amorphous drug compositions, including the water suspension of the amorphous solid dispersion of 5-fluoro-1-(4-fluoro-3-(4-(pyrimidin-2-yl)piperazine-1-carbonyl)benzyl)quinazoline-2,4(1H,3H)-dione. In some embodiments, the water suspensions include an emulsifier, such as methylcellulose, Tween 80. In some embodiments, the water suspension contains the amorphous solid dispersion of 5-fluoro-1-(4-fluoro-3-(4-(pyrimidin-2-yl)piperazine-1-carbonyl)benzyl) quinazoline-2,4(1H,3H)-dione at a concentration of about 1 mg/mL to 100 mg/mL. In some embodiments, the water suspension contains about 0.1% to 2.0% by weight of methylcellulose, such as about 0.5% by weight of methylcellulose.

In some embodiments, the amorphous solid dispersion is obtained by solvent evaporation or spray drying. Therefore, the invention describes the methods for preparing the amorphous solid dispersion of 5-fluoro-1-(4-fluoro-3-(4-(pyrimidin-2-yl)piperazine-1-carbonyl)benzyl)quinazoline-2,4(1H,3H)-dione by spray drying. In some embodiments, the method includes: a) completely dissolving 5-fluoro-1-(4-fluoro-3-(4-(pyrimidin-2-yl)piperazine-1-carbonyl)benzyl) quinazoline-2,4(1H,3H)-dione in a suitable solvent or mixed solvent, then dissolving a moderate amount of polymers or other excipients to get homogeneous solution or suspension; b) spray drying the mixture to obtain an amorphous solid dispersion containing 5-fluoro-1-(4-fluoro-3-(4-(pyrimidin-2-yl)piperazine-1-carbonyl)benzyl)quinazoline-2,4(1H, 3H)-dione. The spray drying can be carried out in the presence of inert gases. In some embodiments, the process of spray drying can be conducted in the presence of the supercritical fluid referring to carbon dioxide or the mixture of carbon dioxide. In some embodiments, the polymer is HPMCP (HP-55), HPC or HPMCAS. In some embodiments, the content of the polymer in the solid dispersion is about 50% to 80% by weight. In some embodiments, the mixture also includes a surfactant, such as Poloxamer or Tween 80.

In some embodiments, the solvents include tetrahydrofuran. In some embodiments, the solvents include methanol. In some embodiments, the solvents include the mixture of tetrahydrofuran and methanol. For example, the solvents may include about 0% to 30% of methanol and about 70% to 100% of tetrahydrofuran. In other exemplary examples, the ratios of tetrahydrofuran and methanol include 80:20, 75:25, and 70:30.

In another aspect, the invention is characterized in the methods for the treatment of cancer in mammal. In one embodiment, the method includes administration of the amorphous solid dispersion of 5-fluoro-1-(4-fluoro-3-(4-(pyrimidin-2-yl)piperazine-1-carbonyl)benzyl)quinazoline-2,4(1H,3H)-dione. In another aspect, the invention is characterized in drug packaging or pill case, which include the amorphous solid dispersion composition of 5-fluoro-1-(4-fluoro-3-(4-(pyrimidin-2-yl)piperazine-1-carbonyl)benzyl) quinazoline-2,4(1H,3H)-dione described herein.

The details of one or more invention implementation ways will be explained in the following. Other characteristics, objects and merits in the invention are obvious because of the specification and claims.

DETAILED DESCRIPTION OF THE INVENTION

In general, it has bee found the bioavailability is very low after oral administration of crystalline 5-fluoro-1-(4-fluoro-3-(4-(pyrimidin-2-yl)piperazine-1-carbonyl)benzyl)quinazoline-2,4(1H,3H)-dione to mice. For example, after oral administration of the simple mixture of crystalline 5-fluoro-1-(4-fluoro-3-(4-(pyrimidin-2-yl)piperazine-1-carbonyl) benzyl)quinazoline-2,4(1H,3H)-dione, conventional surfactants (such as Tween 80), and emulsifiers (such as methylcellulose) to mammals such as mice, the bioavailability of 5-fluoro-1-(4-fluoro-3-(4-(pyrimidin-2-yl)piperazine-1-carbonyl)benzyl)quinazoline-2,4(1H,3H)-dione is less than 5%. Such a low oral absorption cannot reach the drug concentration of 5-fluoro-1-(4-fluoro-3-(4-(pyrimidin-2-yl)piperazine-1-carbonyl)benzyl)quinazoline-2,4(1H, 3H)-dione needed for treatment effect. The solution of 5-fluoro-1-(4-fluoro-3-(4-(pyrimidin-2-yl)piperazine-1-carbonyl)benzyl)quinazoline-2,4(1H,3H)-dione was prepared by using organic solvents such as dimethyl sulfoxide (DMSO) and dimethylformamide (DMF) and adding 2-hydroxypropyl-β-cyclodextrin (HP-β-CD), and it can greatly increase the oral absorption of 5-fluoro-1-(4-fluoro-3-(4-(pyrimidin-2-yl)piperazine-1-carbonyl)benzyl)quinazoline-2,4(1H,3H)-dione. However, DMSO and DMF as organic solvents are not suitable for administration to human. The amorphous solid dispersion composition of 5-fluoro-1-(4-fluoro-3-(4-(pyrimidin-2-yl)piperazine-1-carbonyl)benzyl)quinazoline-2,4(1H,3H)-dione of the present invention can provide higher bioavailability. Therefore some embodiments provide the amorphous solid dispersion formulations of 5-fluoro-1-(4-fluoro-3-(4-(pyrimidin-2-yl)piperazine-1-carbonyl)benzyl)quinazoline-2,4(1H,3H)-dione. In some embodiments, the invention includes the pharmaceutical compositions of the amorphous solid dispersions of 5-fluoro-1-(4-fluoro-3-(4-(pyrimidin-2-yl)piperazine-1-carbonyl)benzyl)quinazoline-2,4(1H,3H)-dione. The compositions of 5-fluoro-1-(4-fluoro-3-(4-(pyrimidin-2-yl)piperazine-1-carbonyl)benzyl)quinazoline-2,4(1H,3H)-dione in this invention are stable and easy for oral administration to mammals, and show very high bioavailability of 5-fluoro-1-(4-fluoro-3-(4-(pyrimidin-2-yl)piperazine-1-carbonyl)benzyl)quinazoline-2,4(1H,3H)-dione after administration.

The term "amorphous" as employed herein refers to a solid material without long-range order in the atomic positions. Generally molecules of the amorphous solid arrange in a random way, so that there is no definite arrangement and no long-range order. Amorphous solids are isotropic in general, that is it shows similar properties in all directions and doesn't have definite melting point. For example, the amorphous material is a solid material without sharp characteristic peaks in its X-ray powder diffraction (XRPD) pattern (that is it is not crystalline according the determination by XRPD).

The term "crystalline solid" is used herein to mean a compound or composition of which the structural units arrange in fixed geometrical patterns or bitmap, so that the crystalline solid has rigid long range order. The unit of the crystal structure can be atoms, molecules or ions. The crystalline solid shows definite melting point. For example, the crystalline solid has sharp characteristic peaks in its X-ray powder diffraction (XRPD) pattern (that is it is crystalline according the determination by XRPD).

The term "dispersion" as used herein means dispersion system, wherein a matter that is the dispersed phase is distributed among the second matter (the continuous phase or carriers) in discrete units. The size of the dispersed phase can be very different (such as the colloid ion with nano size up to multi-micron size). In general, the dispersed phase can be solid, liquid or gas. In the case of solid dispersions, the dispersed phase and the continuous phase are both solids. In the applications of drugs, the solid dispersion may include crystalline drugs (the dispersed phase) in the amorphous polymers (the continuous phase), or dispersions of the amorphous drugs (the dispersed phase) in the amorphous polymers (the continuous phase). In some embodiments, the amorphous solid dispersion includes the drug forming the dispersed phase and the polymer forming the continuous phase.

The term "amorphous solid dispersions" is used herein to generally mean the solid dispersion having two or more components which are usually the drug and the polymer. However, it also can include other components, such as surfactants or other drug excipients, in which the drug is in the amorphous phase. The physical stability and solubility of the amorphous drugs are enhanced by other components.

The amorphous solid dispersion provided herein is especially desirable implementation ways of the invention. The amorphous solid dispersion usually includes the compound dispersed among the suitable carrier medium (such as solid carrier). In one embodiment, the carriers according to the present invention include polymers, preferably water-soluble or partially water-soluble polymers. In the amorphous solid dispersion herein there can be one or more water-soluble polymers. The amorphous solid dispersion herein is commonly in powder form.

The exemplary amorphous solid dispersion is the coprecipitate or eutectic of 5-fluoro-1-(4-fluoro-3-(4-(pyrimidin-2-yl)piperazine-1-carbonyl)benzyl)quinazoline-2,4(1H, 3H)-dione and at least one polymer. "Coprecipitate" is the product obtained by dissolving the drug and the polymer in the solvent or solvent mixture followed by removing the solvent or solvent mixture. Sometimes the drug and the polymer can suspend in the solvent or solvent mixture. The solvent or solvent mixture includes the organic solvent and supercritical fluid. "Eutectic" is the product obtained by heating the drug and the polymer to melt, optionally which is obtained by mixing with the solvent or solvent mixture and removing at least part of the solvent appropriately, then cooling to rt. at the selected rate. In some cases, the solid dispersion is prepared as follow: adding the drug solution and solid polymers, mixing then removing the solvent. Vacuum drying, spray drying, tray drying, freeze-drying and other drying technology can be used to remove the solvent. According to the invention, the amorphous state of 5-fluoro-1-(4-fluoro-3-(4-(pyrimidin-2-yl)piperazine-1-carbonyl)benzyl)quinazoline-2,4(1H,3H)-dione will be obtained from the final solid dispersion product by any of these methods with appropriate processing parameters.

Any method for providing amorphous solid dispersions can be used in the present invention. In general, any of those methods including removing the solvent of the mixture rapidly or cooling the melted sample can be used. This kind of method includes but not limited to rotary evaporation, freeze drying (lyophilization), vacuum drying, melting freezing and melting extrusion. However, the preferred embodiment in the invention refers to the amorphous solid dispersion obtained by spray drying. Therefore in the other embodiment, the invention provides the amorphous solid dispersion product obtained by removing the solvent through spray drying.

The formulations disclosed herein, such as the pharmaceutical composition, can be obtained by spray drying the mixture containing 5-fluoro-1-(4-fluoro-3-(4-(pyrimidin-2-yl)piperazine-1-carbonyl)benzyl)quinazoline-2,4(1H,3H)-dione, suitable polymer and suitable solvent. Spray drying is a method referring to atomization and solvent-removing of liquid mixture containing such as solid and solvent. For example, the atomization can be conducted by a nozzle or in a rotating disk. Spray drying is a method for converting liquid feed into a form of dry particles. The second drying method also can be used, such as fluidized bed drying and vacuum drying, in order to reduce residual solvents to a pharmaceutically acceptable level. Generally, spray drying refers to making a highly dispersed liquid suspension or solution contact with hot air with enough volume, and causing evaporation and drying of droplets. The formulation of spray drying can be any solution, coarse suspension, grout, colloidal dispersion or paste that can be atomized by the choosed spray drying equipment. In the standard process, the formulation is injected into warm filtered air flow to evaporate the solvent, and the dried product is sent to an accumulator (such as cyclone collector). Then the used air and solvent are discharged, or the used air is sent to the condensator and the solvent is intercepted and may be recycled. Spray drying can be conducted by commercially available instruments.

Solid load factor of the material used for spray drying is about 2% to about 30% (that is the drug and polymer), preferably at least about 4%. Generally, the upper limit of solid load factor is limited by the solution viscosity (such as pumping capacity) and the solubility of components in the solution. In general, the solution viscosity has effect on the particle size of powder product.

In general, the inlet temperature for spray drying is about 60° C. to 200° C., such as from about 70° C. to 150° C., preferably from about 80° C. to 110° C., such as about 85° C. The outlet temperature for spray drying is from about 40° C. to 100° C., such as from 50° C. to 65° C., such as about 45° C. Removal of the solvent may further require subsequent drying steps, such as tray drying, fluidized bed drying (such as from about room temperature to about 100° C.), vacuum drying, microwave drying, drum drying or double cone vacuum drying (such as from about room temperature to about 200° C.), such as from about room temperature to about 65° C., such as about 45° C.

In a preferred method, the solvents include volatile solvents. In some embodiments, the solvents include the mixture of volatile solvents. Preferred solvents include the solvents which can dissolve 5-fluoro-1-(4-fluoro-3-(4-(pyrimidin-2-yl)piperazine-1-carbonyl)benzyl)quinazoline-2,4(1H,3H)-dione and the polymer. Suitable solvents include tetrahydrofuran, methanol, etc. In a more preferred method, the solvent is a mixture of tetrahydrofuran and methanol.

The solid dispersions herein include 5-fluoro-1-(4-fluoro-3-(4-(pyrimidin-2-yl)piperazine-1-carbonyl)benzyl)quinazoline-2,4(1H,3H)-dione and polymers (such as solid carriers). In one embodiment, the polymer of the present invention can dissolve in the water medium. The solubility of the polymer can be pH independent or pH dependent. The latter includes one or more enteric soluble polymers. The term "enteric soluble polymer" refers to a polymer which is preferably dissolved in weak acidic environment of intestines compared to strong acidic environment of stomach, such as the polymer unsoluble in acidic aqueous medium whereas soluble at a pH value of above 5~6. Suitable polymers should be chemically and biologically inert. In order to improve the physical stability of the solid dispersion, the glass transition temperature (Tg) of the polymer should be as high as possible. For example, the glass transition temperature of the preferred polymer is at least equal to or greater than that of the drug (such as 5-fluoro-1-(4-fluoro-3-(4-(pyrimidin-2-yl)piperazine-1-carbonyl)benzyl)quinazoline-2,4(1H,3H)-dione). Suitable examples of Tg of the polymer includes at least about 80° C., 90° C., 100° C., 110° C., 120° C., 130° C., 140° C., 150° C., and at least about 160° C. (measured under drying condition). The mechanism is the polymer with higher Tg having lower molecular mobility at rt. usually, which may be a key factor on the physical stability of the amorphous solid dispersion.

In one embodiment, the polymer is one or more water-soluble or partially water-soluble polymers. Water-soluble or partially water-soluble polymers include but not limited to cellulose derivative (such as hydroxypropyl methyl cellulose (HPMC), hydroxy propyl cellulose (HPC), or ethylcellulose); polyvinylpyrrolidone (PVP); polyethylene glycol (PEG); polyvinyl alcohol (PVA); acrylic ester, such as polymethacrylate (such as PAMA); cyclodextrin (such as β-cyclodextrin), and the copolymers and derivatives thereof, such as polyvinylpyrrolidone-vinyl acetate (PVP-VA). In some preferred embodiments, the polymer is hydroxypropyl methyl cellulose (HPMC), such as HPMCE50 or HPMCE15. In some preferred embodiments, the polymer is Eudragit. Just as what discussed herein, the polymer can be pH dependent enteric soluble polymers. This kind of pH dependent enteric soluble polymers include but not limited to cellulose derivatives (such as cellulose acetate phthalate (CAP)), hydroxypropyl methyl cellulose phthalate (HPMCP, also known as phthalic acid hydroxypropyl methyl cellulose (HP-55))), hydroxypropyl methyl cellulose succinate acetate (HPMCAS), carboxymethylcellulose (CMC) or its salt (such as sodium salt, such as CMC-Na); cellulose acetate trimellitate (CAT), hydroxypropyl cellulose acetate phthalate (HP-CAP), hydroxypropyl methyl cellulose acetate phthalate (HPMCAP) and Methyl cellulose acetate phthalate (MCAP), or polymethacrylate (such as PAMA). In some preferred embodiments, the polymer is Eudragit, hydroxy propyl cellulose (HPC), hydroxypropyl methyl cellulose acetate succinate (HPMCAS), or hydroxypropyl methylcellulose phthalate (HPMCP, HP-55). In more preferred embodiment, the polymer is hydroxypropyl methyl cellulose acetate succinate (HPMCAS) or hydroxypropyl methylcellulose phthalate (HPMCP, HP-55).

In an embodiment wherein the solid dispersion is prepared from the drug and polymer (such as 5-fluoro-1-(4-fluoro-3-(4-(pyrimidin-2-yl)piperazine-1-carbonyl)benzyl)quinazoline-2,4(1H,3H)-dione and HPMC or HPMCAS polymer), the content of the polymer usually is about 40~80% by weight relative to the total weight of the solid dispersion. The content usually is about 80% or less, preferably 75% or less, about 70% or less. In one embodiment, the amount of the polymer accounts for up to about 79% of total weight of the dispersion (in turn more specifically, between about 71% to 79%, such as about 71%, about 73%, about 75%, about 77%, or about 79%). In one of a variety of specific embodiments of the invention, the polymer is hydroxypropyl methylcellulose phthalate (HPMCP) (such as HP-55), and the content thereof is about 75%. Just as what disclosed herein, the invention includes the dispersion containing about 75% of HP-55.

In the embodiments including polymers, the content of the polymer should stabilize the solid dispersion effectively. Stabilization includes inhibiting or preventing crystallization of 5-fluoro-1-(4-fluoro-3-(4-(pyrimidin-2-yl)piperazine-1-carbonyl)benzyl)quinazoline-2,4(1H,3H)-dione. The kind of stabilization will inhibit the conversion of 5-fluoro-1-(4-fluoro-3-(4-(pyrimidin-2-yl)piperazine-1-carbonyl)benzyl)quinazoline-2,4(1H,3H)-dione from amorphous state to crystalline form. For example, the polymer will prevent at least a part (such as about 1%, about 3%, about 5%, about 10%, or more) of 5-fluoro-1-(4-fluoro-3-(4-(pyrimidin-2-yl)piperazine-1-carbonyl)benzyl)quinazoline-2,4(1H,3H)-dione converting from amorphous state to crystalline form. Stabilization can be measured as follows such as measuring the glass transition temperature of the amorphous solid dispersion, measuring the crystallinity of the amorphous solid dispersion (XRPD), or measuring the dissolution rate and solubility, bioavailability of the amorphous solid dispersion of 5-fluoro-1-(4-fluoro-3-(4-(pyrimidin-2-yl)piperazine-1-carbonyl)benzyl)quinazoline-2,4(1H,3H)-dione. It also can be observed by using polarizing microscope (PLM), differential thermal analysis (DSC), and spectral instruments (such as infrared, Raman).

The polymer should have a solubility similar to or better than 5-fluoro-1-(4-fluoro-3-(4-(pyrimidin-2-yl)piperazine-1-carbonyl)benzyl)quinazoline-2,4(1H,3H)-dione in the solvent suitable for spray drying process. In a preferred embodiment, the polymer will dissolve in one or more same solvents or solvent systems as 5-fluoro-1-(4-fluoro-3-(4-(pyrimidin-2-yl)piperazine-1-carbonyl)benzyl)quinazoline-2,4(1H,3H)-dione. Preferably, the polymer can dissolve in tetrahydrofuran, methanol, or a mixed solvent of tetrahydrofuran and methanol.

Solid dispersions or other compositions can include surfactants. Surfactants or the mixture of surfactants will reduce the interfacial tension between solid dispersions and water medium. Appropriate surfactants or the mixture of surfactants also can enhance the water solubility and bioavailability from the solid dispersion of 5-fluoro-1-(4-fluoro-3-(4-(pyrimidin-2-yl)piperazine-1-carbonyl)benzyl)quinazoline-2,4(1H,3H)-dione. Surfactants used in the invention include but not limit to sorbitan fatty acid ester (such as span), polyoxyethylene sorbitan fatty acid ester (e.g., tween), sodium lauryl sulfate (SLS), sodium dodecyl benzene sulfonate (SDBS), dioctyl sulfosuccinate sodium (Docusate), dihydroxy bile acid sodium salt (DOSS), sorbitan monostearate, sorbitan tristearate, cetyltrimethylammonium bromide (CTAB), N-lauroyl sarcosine sodium, sodium oleate, sodium myristate, sodium stearate and sodium palmitate, Gelucire 44/14, ethylene diamine tetraacetic acid (EDTA), vitamin E, d-α tocopherol, polyethylene glycol (peg) 1000, succinic acid ester (TPGS), lecithin, MW 677-692, L(+)-Monosodium glutamate monohydrate, Labrasol, PEG 8, caprylyl/capryl glyceride, transcutol, diethylene glycol monoethyl ether, Solutol HS-15, polyethylene glycol (peg)/hydroxy stearate, taurocholic acid, Pluronic F68, Pluronic F108 and Pluronic F127 (or any other polyoxyethylene-polyoxypropylene copolymer or saturated polyethylene glycol (peg) glyceride), Tween 80 and Poloxamer 188. Tween 80 and Poloxamer 188 are preferred.

The present invention also provides a therapeutic method comprising administering to a mammal an effective amount of the amorphous solid dispersion of 5-fluoro-1-(4-fluoro-3-(4-(pyrimidin-2-yl)piperazine-1-carbonyl)benzyl)quinazoline-2,4(1H,3H)-dione, wherein said therapeutic method is useful for the treatment of diseases due to abnormal PARP activity, such as cancer. Such diseases that can be treated or prevented by the method or pharmaceutical composition of the present invention include, but are not limited to, liver cancer, melanoma, Hodgkin's disease, non-Hodgkin's lymphoma, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head or neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

Formulations of the present invention also are useful for the treatment or prevention of other clinical conditions due to abnormal PARP activity, such as excessive cell death, including central nervous system diseases such as stroke and neurodegenerative diseases.

Another embodiment of the present invention is directed to a composition effective to inhibit neoplasia comprising an amorphous solid dispersion of 5-fluoro-1-(4-fluoro-3-(4-(pyrimidin-2-yl)piperazine-1-carbonyl)benzyl)quinazoline-2,4(1H,3H)-dione, in combination with at least one known anticancer agent or a pharmaceutically acceptable salt thereof. Examples of known anticancer agents which may be used for combination therapy include, but not limited to alkylating agents, such as busulfan, melphalan, chlorambucil, cyclophosphamide, ifosfamide, temozolomide, bendamustine, cis-platin, mitomycin C, bleomycin, and carboplatin; topoisomerase I inhibitors, such as camptothecin, irinotecan, and topotecan; topoisomerase II inhibitors, such as doxorubicin, epirubicin, aclarubicin, mitoxantrone, elliptinium and etoposide; RNA/DNA antimetabolites, such as 5-azacytidine, gemcitabine, 5-fluorouracil and methotrexate; DNA antimetabolites, such as 5-fluoro-2'-deoxy-uridine, fludarabine, nelarabine, ara-C, alanosine, pralatrexate, pemetrexed, hydroxyurea and thioguanine; antimitotic agents, such as colchicine, vinblastine, vincristine, vinorelbine, paclitaxel, ixabepilone, cabazitaxel, and docetaxel; antibodies, such as campath, Panitumumab, Ofatumumab, Avastin, HERCEPTIN (trastuzumab), RITUXAN (rituximab); kinase inhibitors such as imatinib, gefitinib, erlotinib, lapatinib, sorafenib, sunitinib, nilotinib, dasatinib, pazopanib, temsirolimus and everolimus; HDAC inhibitors such as vorinostat and romidepsin. Other known anticancer agents which may be used for combination therapy include tamoxifen, letrozole, fulvestrant, mitoguazone, octreotide, retinoic acid, arsenic trioxide, zoledronic acid, bortezomib, thalidomide and lenalidomide.

In practicing the methods of the present invention, the amorphous solid dispersion of 5-fluoro-1-(4-fluoro-3-(4-(pyrimidin-2-yl)piperazine-1-carbonyl)benzyl)quinazoline-2,4(1H,3H)-dione of the invention may be administered together with at least one known anticancer agent as part of a unitary pharmaceutical composition. Alternatively, the solid dispersion of the invention may be administered apart from at least one known anticancer agent. In one embodiment, the solid dispersion of the invention and at least one known anticancer agent are administered substantially simultaneously, i.e. the compounds are administered at the same time or one after the other, so long as the compounds reach therapeutic levels in the blood at the same time. In another embodiment, the solid dispersion of the invention and at least one known anticancer agent are administered according to their individual dose schedule, so long as the compounds reach therapeutic levels in the blood.

Similarly, another embodiment of the present invention is directed to a pharmaceutical composition effective to inhibit neoplasia comprising an amorphous solid dispersion of 5-fluoro-1-(4-fluoro-3-(4-(pyrimidin-2-yl)piperazine-1-carbonyl)benzyl)quinazoline-2,4(1H,3H)-dione, in combination with radiation therapy. In this embodiment, the solid dispersion of the invention may be administered at the same time as the radiation therapy is administered or at a different time.

Yet another embodiment of the present invention is directed to a pharmaceutical composition effective for postsurgical treatment of cancer, comprising an amorphous solid dispersion of 5-fluoro-1-(4-fluoro-3-(4-(pyrimidin-2-yl)piperazine-1-carbonyl)benzyl)quinazoline-2,4(1H,3H)-dione. The invention also relates to a method of treating cancer by surgically removing the cancer and then treating the mammal with the amorphous solid dispersion of 5-fluoro-1-(4-fluoro-3-(4-(pyrimidin-2-yl)piperazine-1-carbonyl)benzyl)quinazoline-2,4(1H,3H)-dione described herein.

Pharmaceutical compositions within the scope of this invention include all compositions wherein the amorphous solid dispersions of 5-fluoro-1-(4-fluoro-3-(4-(pyrimidin-2-yl)piperazine-1-carbonyl)benzyl)quinazoline-2,4(1H,3H)-dione of the present invention are contained in an amount that is effective to achieve its intended purpose. While individual needs vary, determination of optimal ranges of effective amounts of each component is within the skill of the art. Typically, the solid dispersions may be administered to mammals, orally at a dose of 0.0025 to 50 mg/kg of body weight, per day, to a mammal being treated. Preferably, approximately 0.01 to approximately 10 mg/kg of body weight is orally administered. If a known anticancer agent is also administered, it is administered in an amount that is effective to achieve its intended purpose. The amounts of such known anticancer agents effective for cancer are well known to those skilled in the art.

The unit oral dose may comprise from approximately 0.01 to approximately 50 mg, preferably approximately 0.1 to approximately 10 mg of the solid dispersion of the invention. The unit dose may be administered one or more times daily, as one or more tablets, each containing from approximately 0.1 to approximately 50 mg, conveniently approximately 0.25 to 10 mg of the solid dispersion of the invention.

The pharmaceutical preparations of the invention may be administered to any mammal, which may experience the beneficial effects of the solid dispersions of the invention. Foremost among such mammals are humans and veterinary animals, although the invention is not intended to be so limited.

Other pharmaceutical preparations, which may be used orally, include push-fit capsules made of gelatin. The push-fit capsules may contain the solid dispersions of the invention, which may be mixed with fillers, such as lactose; binders, such as starches; and/or lubricants, such as talc or magnesium stearate and stabilizers.

The following examples are illustrative, but not limiting, of the method and preparations of the present invention. Other suitable modifications and adaptations of the variety of conditions and parameters normally encountered in clinical therapy and which are obvious to those skilled in the art are within the spirit and scope of the invention.

EXAMPLES

5-Fluoro-1-(4-fluoro-3-(4-(pyrimidin-2-yl)piperazine-1-carbonyl)benzyl)quinazoline-2,4(1H,3H)-dione can be prepared by the known methods to those skilled in the art (i.e. by using the process as per Example 132 of WO2012130166A1).

Example 1

Preparation of Amorphous Solid Dispersions Including 5-fluoro-1-(4-fluoro-3-(4-(pyrimidin-2-yl) piperazine-1-carbonyl)benzyl)quinazoline-2,4(1H, 3H)-dione and HPMCAS (Weight Ratio, 1:1, 1:2, and 1:3)

Figure 1:
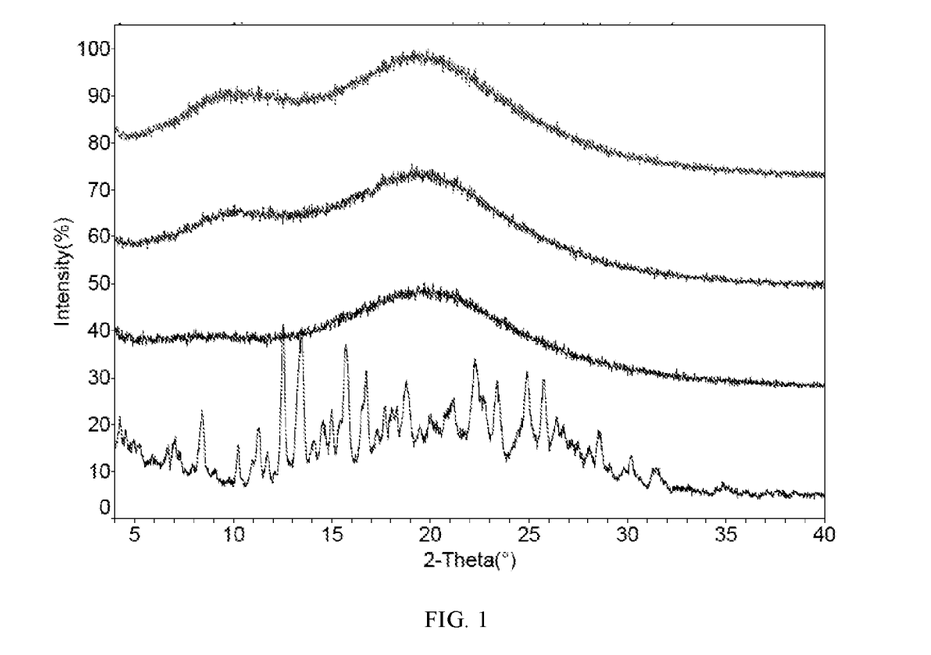
FIG. 1 is the X-ray powder diffraction (XRPD) patterns of the solid dispersions comprising 5-fluoro-1-(4-fluoro-3-(4-(pyrimidin-2-yl)piperazine-1-carbonyl)benzyl)quinazoline-2,4(1H,3H)-dione and HPMCAS (from top to bottom, the ratio is 1:3, 1:2, and 1:1, respectively) after vacuum drying at 45° C. for 3 days. The data show three kinds of solid dispersions are all amorphous, whereas 5-fluoro-1-(4-fluoro-3-(4-(pyrimidin-2-yl)piperazine-1-carbonyl)benzyl) quinazoline-2,4(1H,3H)-dione is crystalline (at the bottom).

About 200 mg of 5-fluoro-1-(4-fluoro-3-(4-(pyrimidin-2-yl)piperazine-1-carbonyl)benzyl)quinazoline-2,4(1H,3H)-dione was dissolved in 57 mL of THF and then HPMCAS was added into the THF solution at different weight ratio (1:1, 1:2 and 1:3). Then the solutions were spray dried using ProCepT 4M8-Trix spray dryer to obtain a solid dispersion. After spray drying, the product was examined using XRPD, PLM, MDSC and TGA. The solid dispersion was also analyzed by HPLC to check its chemical purity and drug loading. Based on the results of XRPD (FIG. 1) and PLM, amorphous materials were formed after spray drying process, including 5-fluoro-1-(4-fluoro-3-(4-(pyrimidin-2-yl) piperazine-1-carbonyl)benzyl)quinazoline-2,4(1H,3H)-dione and HPMCAS at different weight ratio of 1:1, 1:2, and 1:3, whereas 5-fluoro-1-(4-fluoro-3-(4-(pyrimidin-2-yl)piperazine-1-carbonyl)benzyl)quinazoline-2,4(1H,3H)-dione was crystalline.

Example 5

Preparation of Amorphous Solid Dispersions Including 5-fluoro-1-(4-fluoro-3-(4-(pyrimidin-2-yl) piperazine-1-carbonyl)benzyl)quinazoline-2,4(1H, 3H)-dione and Eudragit (Weight Ratio, 1:1, 1:2, and 1:3)

Figure 2:
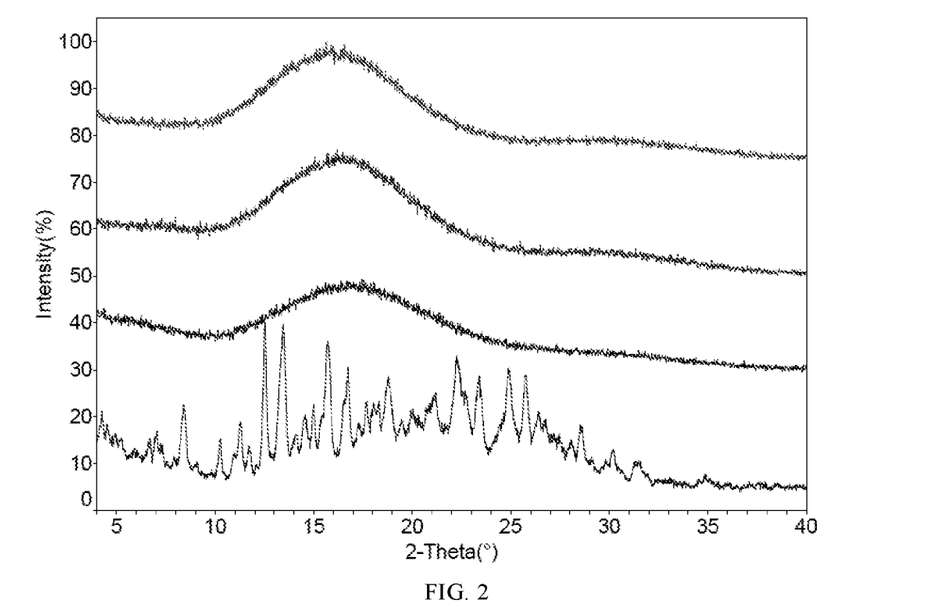
FIG. 2 is the X-ray powder diffraction (XRPD) patterns of the solid dispersions comprising 5-fluoro-1-(4-fluoro-3-(4-(pyrimidin-2-yl)piperazine-1-carbonyl)benzyl)quinazoline-2,4(1H,3H)-dione and Eudragit (from top to bottom, the ratio is 1:3, 1:2, and 1:1, respectively) after vacuum drying at 45° C. for 3 days. The data show three kinds of solid dispersions are all amorphous, whereas 5-fluoro-1-(4-fluoro-3-(4-(pyrimidin-2-yl)piperazine-1-carbonyl)benzyl) quinazoline-2,4(1H,3H)-dione is crystalline (at the bottom).

About 200 mg of 5-fluoro-1-(4-fluoro-3-(4-(pyrimidin-2-yl)piperazine-1-carbonyl)benzyl)quinazoline-2,4(1H,3H)-dione was dissolved in 57 mL of THF and then Eudragit L100 was added into the THF solution at different weight ratio (1:1, 1:2 and 1:3). Then the solutions were spray dried using ProCepT 4M8-Trix spray dryer to obtain a solid dispersion. After spray drying, the product was examined using XRPD, PLM, MDSC and TGA. The solid dispersion was also analyzed by HPLC to check its chemical purity and drug loading. Based on the results of XRPD (FIG. 2) and PLM, amorphous materials were formed after spray drying process, including 5-fluoro-1-(4-fluoro-3-(4-(pyrimidin-2-yl)-yl)piperazine-1-carbonyl)benzyl)quinazoline-2,4(1H,3H)-dione and Eudragit at different weight ratio of 1:1, 1:2, and 1:3.

Example 3

Preparation of Amorphous Solid Dispersion Including 5-fluoro-1-(4-fluoro-3-(4-(pyrimidin-2-yl)piperazine-1-carbonyl)benzyl)quinazoline-2,4(1H,3H)-dione and HPMCAS (Weight Ratio, 1:3)

1.5 g of 5-fluoro-1-(4-fluoro-3-(4-(pyrimidin-2-yl)piperazine-1-carbonyl)benzyl)quinazoline-2,4(1H,3H)-dione was dissolved in 150 mL solvent (MeOH:THF=3:7) (10 mg/mL). Then HPMCAS was added into the solution with the w/w ratio 1:3 (API:HPMCAS) to dissolve. The solution was spray dried to form a solid dispersion on ProCepT 4M8-Trix spray dryer. After vacuum drying at 40° C. for 4 days, the product was examined using PLM, XRPD, TGA-MS and MDSC. The results of PLM and MDSC showed the solid dispersion was amorphous. 0.5% Weight loss was found from rt. to 140° C. by TGA, wherein most of the residue solvent was water. MDSC showed its $T_g$ was about at 99.5° C.

Example 4

Preparation of Amorphous Solid Dispersion Including 5-fluoro-1-(4-fluoro-3-(4-(pyrimidin-2-yl)piperazine-1-carbonyl)benzyl)quinazoline-2,4(1H,3H)-dione and HPC (Weight Ratio, 1:3)

Figure 3:
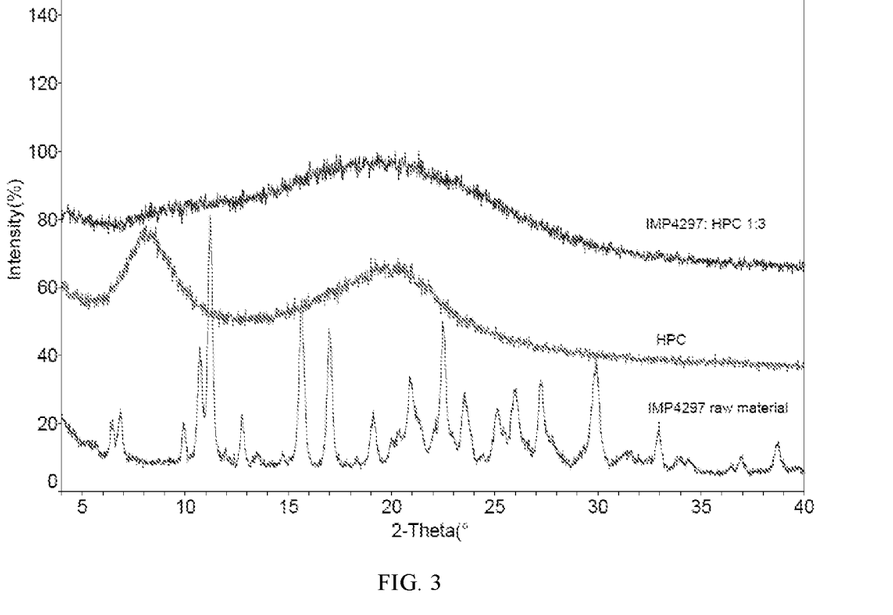
FIG. 3 is the X-ray powder diffraction (XRPD) pattern of the amorphous solid dispersion comprising 5-fluoro-1-(4-fluoro-3-(4-(pyrimidin-2-yl)piperazine-1-carbonyl)benzyl) quinazoline-2,4(1H,3H)-dione and HPC (the ratio is 1:3, at the top). The data show the solid dispersion is amorphous, whereas 5-fluoro-1-(4-fluoro-3-(4-(pyrimidin-2-yl)piperazine-1-carbonyl)benzyl)quinazoline-2,4(1H,3H)-dione is crystalline (at the bottom).

1.5 g of 5-fluoro-1-(4-fluoro-3-(4-(pyrimidin-2-yl)piperazine-1-carbonyl)benzyl)quinazoline-2,4(1H,3H)-dione was dissolved in 150 mL solvent (MeOH:THF=3:7). After completely dissolved and filtered, HPC was added into the solution with the w/w ratio 1:3 (API:HPC) to dissolve. The solution was spray dried to form a solid dispersion. After vacuum drying at 30° C. for 4 days, the product was examined using PLM, XRPD, TGA-MS and MDSC. The results of PLM and XRPD (FIG. 3) showed the solid dispersion was amorphous. TGA-MS showed there was some residual water. MDSC showed its $T_g$ was about at 62.9° C.

The amorphous solid dispersions of Examples 5, 6, and 7 were prepared using a method similar to that used for Example 4.

Example 5

Preparation of Amorphous Solid Dispersion Including 5-fluoro-1-(4-fluoro-3-(4-(pyrimidin-2-yl)piperazine-1-carbonyl)benzyl)quinazoline-2,4(1H,3H)-dione and HPMCP (HP-55) (Weight Ratio, 1:3)

Figure 4:
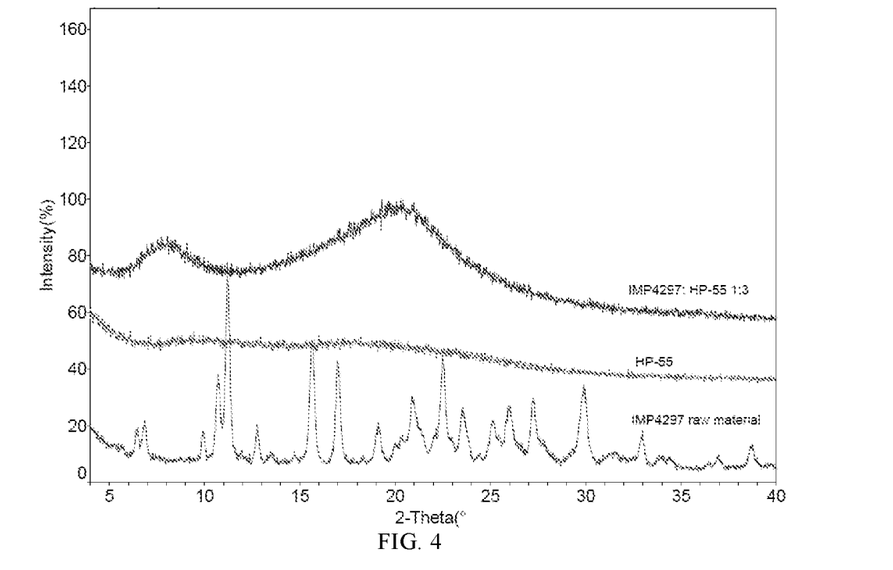
FIG. 4 is the X-ray powder diffraction (XRPD) pattern of the solid dispersion comprising 5-fluoro-1-(4-fluoro-3-(4-(pyrimidin-2-yl)piperazine-1-carbonyl)benzyl)quinazoline-2,4(1H,3H)-dione and HPMCP (HP-55) (the ratio is 1:3, at the top). The data show the solid dispersion is amorphous, whereas 5-fluoro-1-(4-fluoro-3-(4-(pyrimidin-2-yl)piperazine-1-carbonyl)benzyl)quinazoline-2,4(1H,3H)-dione is crystalline (at the bottom).

Based on results of PLM, XRPD (FIG. 4) and DSC, the solid dispersion product (5-fluoro-1-(4-fluoro-3-(4-(pyrimidin-2-yl)piperazine-1-carbonyl)benzyl)quinazoline-2,4(1H,3H)-dione:HP-55 1:3) was amorphous. MDSC showed its $T_g$ was about at 96.8° C.

Example 6

Preparation of Amorphous Solid Dispersion Including 5-fluoro-1-(4-fluoro-3-(4-(pyrimidin-2-yl)piperazine-1-carbonyl)benzyl)quinazoline-2,4(1H,3H)-dione and HPMCP (HP-55) (Weight Ratio, 1:2)

Based on results of PLM, XRPD and DSC, the solid dispersion product (5-fluoro-1-(4-fluoro-3-(4-(pyrimidin-2-yl)piperazine-1-carbonyl)benzyl)quinazoline-2,4(1H,3H)-dione:HP-55 1:2) was amorphous. MDSC showed its $T_g$ was about at 80.0° C.

Example 7

Preparation of Amorphous Solid Dispersion Including 5-fluoro-1-(4-fluoro-3-(4-(pyrimidin-2-yl)piperazine-1-carbonyl)benzyl)quinazoline-2,4(1H,3H)-dione, HPMCP (HP-55), and Poloxamer 188 (Weight Ratio, 1:2.8:0.2)

Based on results of PLM, XRPD and DSC, the solid dispersion product (5-fluoro-1-(4-fluoro-3-(4-(pyrimidin-2-yl)piperazine-1-carbonyl)benzyl)quinazoline-2,4(1H,3H)-dione:HP-55:Poloxamer 1:2.8:0.2) was amorphous. MDSC showed its $T_g$ was about at 78.8° C.

Example 8

Measurement of the Effects of 5-fluoro-1-(4-fluoro-3-(4-(pyrimidin-2-yl)piperazine-1-carbonyl)benzyl)quinazoline-2,4(1H,3H)-dione Vehicle Formulas on the Drug Absorption Using a Mouse Pharmacokinetics (PK) Method 5-Fluoro-1-(4-fluoro-3-(4-(pyrimidin-2-yl)piperazine-1-carbonyl)benzyl)quinazoline-2,4(1H,3H)-dione in different vehicle formulas at the same dosage was administered to ICR mice by gavage. The blood was sampled at 30 min after gavage, the blood concentrations were measured by LCMS method, and the effects on the drug absorption of different vehicle formulas was made a comparison. The blood concentrations were shown as the table below:

| Group | | Blood Concentration (ng/ml) |
|---|---|---|
| Formula 1 | 2% Tween 80, 0.5% MC in water, emulsion | 211 |
| Formula 2 | DMF:Tween 80:10% HP-β-CD PBS = 10:2:88, solution | 2151 |
| Formula 3 | DMSO:10% HP-β-CD PBS = 1:9, solution | 1365 |
| Formula 4 | DMA:20% HP-β-CD PBS = 1:9, solution | 590 |
| Formula 5 | DMF:Tween 80:20% HP-β-CD PBS = 10:2:88, solution | 2769 |

The results showed the oral absorption of the emulsion of 0.5% MC and 2% Tween 80 was very poor due to the very low water solubility of 5-fluoro-1-(4-fluoro-3-(4-(pyrimidin-2-yl)piperazine-1-carbonyl)benzyl)quinazoline-2,4(1H, 3H)-dione. The oral absorption can be enhanced when 5-fluoro-1-(4-fluoro-3-(4-(pyrimidin-2-yl)piperazine-1-carbonyl)benzyl)quinazoline-2,4(1H,3H)-dione was prepared into a solution by using DMSO and DMF (10%) as solvent with the addition of 2-hydroxypropyl-β-cyclodextrin (HP-β-CD), which can be improved more than 10 times compared with the emulsion. For example, the oral absorption rate was 48% when ICR mice received the solution of 5-fluoro-1-(4-fluoro-3-(4-(pyrimidin-2-yl)piperazine-1-carbonyl)benzyl)quinazoline-2,4(1H,3H)-dione in DMSO: 10% HP-β-CD PBS=1:9 by gavage. However, DMSO and DMF as organic solvents are not suitable for administration to human.

Example 9

Preparation of Oral Formulation of the Amorphous Solid Dispersion Aqueous Suspension (0.5% MC/water) of 5-fluoro-1-(4-fluoro-3-(4-(pyrimidin-2-yl)piperazine-1-carbonyl)benzyl)quinazoline-2,4 (1H,3H)-dione The amorphous solid dispersion of 5-fluoro-1-(4-fluoro-3-(4-(pyrimidin-2-yl)piperazine-1-carbonyl)benzyl)quinazoline-2,4(1H,3H)-dione and a fraction of 0.5% MC/water were mixed in a mortar, and grinded for 1~2 min to form homogeneous slurry. Remnants of 0.5% MC/water were added into the above mortar and the mixture was grinded for additional 1 min to form a homogeneous slurry with the target concentration, as the oral formulation for the animal study.

Example 10

Measurement of the Absorption Ratio of the Amorphous Solid Dispersion Compositions of 5-fluoro-1-(4-fluoro-3-(4-(pyrimidin-2-yl)piperazine-1-carbonyl)benzyl)quinazoline-2,4(1H,3H)-dione Using a Mouse Pharmacokinetics (PK) Method The amorphous solid dispersion compositions of 5-fluoro-1-(4-fluoro-3-(4-(pyrimidin-2-yl)piperazine-1-carbonyl)benzyl)quinazoline-2,4(1H,3H)-dione were prepared into homogeneous suspensions in 0.5% MC/water using a method similar to that used for Example 9. ICR mice were received different compositions of 5-fluoro-1-(4-fluoro-3-(4-(pyrimidin-2-yl)piperazine-1-carbonyl)benzyl)quinazoline-2,4(1H,3H)-dione by gavage. The blood was sampled at a certain time after administration. The blood concentrations were measured by LCMS method, and the effects on the drug absorption of different compositions of 5-fluoro-1-(4-fluoro-3-(4-(pyrimidin-2-yl)piperazine-1-carbonyl)benzyl)quinazoline-2,4(1H,3H)-dione were made a comparison by a mouse pharmacokinetics (PK) measurement. The results were shown in the following table:

| Amorphous solid dispersions | Dosage mg/kg | $AUC_{0-t}$ ng · h/mL | $AUC_{0-\infty}$ ng · h/mL | $t_{1/2}$ h | $C_{max}$ ng/mL |
|---|---|---|---|---|---|
| 5-Fluoro-1-(4-fluoro-3-(4-(pyrimidin-2-yl)piperazine-1-carbonyl)benzyl)quinazoline-2,4(1H,3H)-dione:HPMCAS (1:3) | 10 | 2430 | 2663 | 2.68 | 2113 |
| 5-Fluoro-1-(4-fluoro-3-(4-(pyrimidin-2-yl)piperazine-1-carbonyl)benzyl)quinazoline-2,4(1H,3H)-dione:HPC (1:3) | 10 | 1495 | 1544 | 1.19 | 622 |
| 5-Fluoro-1-(4-fluoro-3-(4-(pyrimidin-2-yl)piperazine-1-carbonyl)benzyl)quinazoline-2,4(1H,3H)-dione:HP-55 (1:3) | 12.3 | 11741 | 11786 | 1.77 | 11463 |
| 5-Fluoro-1-(4-fluoro-3-(4-(pyrimidin-2-yl)piperazine-1-carbonyl)benzyl)quinazoline-2,4(1H,3H)-dione:HP-55 (1:2) | 13.5 | 7369 | 7500 | 1.36 | 8860 |
| 5-Fluoro-1-(4-fluoro-3-(4-(pyrimidin-2-yl)piperazine-1-carbonyl)benzyl)quinazoline-2,4(1H,3H)-dione:HP-55:poloxamer (1:2.8:0.2) | 12.6 | 8445 | 8732 | 1.60 | 10673 |

The results showed the oral absorption rate after gavage was very good when the homogeneous suspension in 0.5% MC/water was prepared from the amorphous solid dispersion of 5-fluoro-1-(4-fluoro-3-(4-(pyrimidin-2-yl)piperazine-1-carbonyl)benzyl)quinazoline-2,4(1H,3H)-dione, wherein the oral absorption rate of the amorphous solid dispersion of 5-fluoro-1-(4-fluoro-3-(4-(pyrimidin-2-yl)piperazine-1-carbonyl)benzyl)quinazoline-2,4(1H,3H)-dione:HP-55 (1:3) was best. Therefore, the oral absorption of 5-fluoro-1-(4-fluoro-3-(4-(pyrimidin-2-yl)piperazine-1-carbonyl)benzyl)quinazoline-2,4(1H,3H)-dione can be greatly enhanced when prepared into an amorphous solid dispersion.

Example 11

Measurement of the Absorption Ratio of the Amorphous Solid Dispersions of 5-fluoro-1-(4-fluoro-3-(4-(pyrimidin-2-yl)piperazine-1-carbonyl)benzyl)quinazoline-2,4(1H,3H)-dione:HP-55 (1:3) Using a Mouse Pharmacokinetics (PK) Method The solution of 5-fluoro-1-(4-fluoro-3-(4-(pyrimidin-2-yl)piperazine-1-carbonyl)benzyl)quinazoline-2,4(1H,3H)-dione in DMSO: 10% HP-β-CD PBS (1:9) was administered to mice at 1 mg/kg by IV. And the homogeneous suspension of the amorphous solid dispersion of 5-fluoro-1-(4-fluoro-3-(4-(pyrimidin-2-yl)piperazine-1-carbonyl)benzyl)quinazoline-2,4(1H,3H)-dione:HP-55 (1:3) in 0.5% MC/water was administered to mice at 10 mg/kg by IG. The blood was sampled at a certain time after administration. The blood concentrations were measured by LCMS method, and the oral absorption was measured by a mouse pharmacokinetics (PK) method. The results were shown in the following table:

| Group | Dosage mg/kg | $AUC_{0-t}$ ng · h/mL | $AUC_{0-\infty}$ ng · h/mL | $t_{1/2}$ h | $C_{max}$ ng/mL | Oral absorption rate (F %) |
|---|---|---|---|---|---|---|
| IV | 1 | 991 | 997 | 0.545 | 1916 | |
| IG | 10 | 4168 | 4184 | 1.05 | 6617 | 42% |

The results showed the oral absorption rate of the amorphous solid dispersion of 5-fluoro-1-(4-fluoro-3-(4-(pyrimidin-2-yl)piperazine-1-carbonyl)benzyl)quinazoline-2,4(1H, 3H)-dione:HP-55 (1:3) in mice was 42%. Therefore, the oral absorption rate in mice of the amorphous solid dispersion of 5-fluoro-1-(4-fluoro-3-(4-(pyrimidin-2-yl)piperazine-1-carbonyl)benzyl)quinazoline-2,4(1H,3H)-dione is similar to that of the solution formulation of 5-fluoro-1-(4-fluoro-3-(4-(pyrimidin-2-yl)piperazine-1-carbonyl)benzyl)quinazoline-2,4(1H,3H)-dione in DMSO/DMF and HP-β-CD.

Example 12

Measurement of the Absorption Ratio of the Amorphous Solid Dispersions of 5-fluoro-1-(4-fluoro-3-(4-(pyrimidin-2-yl)piperazine-1-carbonyl)benzyl)quinazoline-2,4(1H,3H)-dione:HP-55 (1:3) Using a Rat Pharmacokinetics (PK) Method The solution of 5-fluoro-1-(4-fluoro-3-(4-(pyrimidin-2-yl)piperazine-1-carbonyl)benzyl)quinazoline-2,4(1H,3H)- dione in DMSO: 10% HP-β-CD PBS (1:9) was administered to Wistar rats at 1 mg/kg by IV. And the homogeneous suspension of the amorphous solid dispersion of 5-fluoro-1-(4-fluoro-3-(4-(pyrimidin-2-yl)piperazine-1-carbonyl)benzyl)quinazoline-2,4(1H,3H)-dione:HP-55 (1:3) in 0.5% MC/water was administered to Wistar rats at 10 mg/kg by IG. The blood was sampled at a certain time after administration. The blood concentrations were measured by LCMS method, and the oral absorption was measured by a rat pharmacokinetics (PK) method. The results were shown in the following table:

| Group | Dosage mg/kg | $AUC_{0-t}$ ng · h/mL | $AUC_{0-\infty}$ ng · h/mL | $t_{1/2}$ h | $C_{max}$ ng/mL | Oral absorption rate (F %) |
|---|---|---|---|---|---|---|
| Male (IG) | 10 | 935 | 948 | 4.57 | 709 | 26.0% |
| Male (IV) | 1 | 363 | 365 | 0.85 | 896 | |
| Female (IG) | 10 | 8117 | 8232 | 4.29 | 2467 | 63.7% |
| Female (IV) | 1 | 1252 | 1292 | 5.06 | 618 | |

The results showed the oral absorption rate of the amorphous solid dispersion of 5-fluoro-1-(4-fluoro-3-(4-(pyrimidin-2-yl)piperazine-1-carbonyl)benzyl)quinazoline-2,4(1H,3H)-dione:HP-55 (1:3) in Wistar male rats was 26%, and the oral absorption rate in Wistar female rats was 63.7%. The oral absorption rate in female was higher than male.

Example 13

Measurement of the Absorption Ratio of the Amorphous Solid Dispersions of 5-fluoro-1-(4-fluoro-3-(4-(pyrimidin-2-yl)piperazine-1-carbonyl)benzyl)quinazoline-2,4(1H,3H)-dione:HP-55 (1:3) Using a Dog Pharmacokinetics (PK) Method The homogeneous suspension of the amorphous solid dispersion of 5-fluoro-1-(4-fluoro-3-(4-(pyrimidin-2-yl)piperazine-1-carbonyl)benzyl)quinazoline-2,4(1H,3H)-dione:HP-55 (1:3) in 0.5% MC/water was administered to Bergle male dogs at 3 mg/kg by IG. The blood was sampled at a certain time after administration. The blood concentrations were measured, and the oral absorption was measured by a dog pharmacokinetics (PK) method. The results were shown in the following table:

| Group | Dosage mg/kg | $AUC_{0-t}$ ng · h/mL | $AUC_{0-\infty}$ ng · h/mL | $t_{1/2}$ h | $C_{max}$ ng/mL | Oral absorption rate (F %) |
|---|---|---|---|---|---|---|
| Male (IG) | 3 | 2820 | 2870 | 3.90 | 828 | 51.9% |

The results showed the oral absorption rate of the amorphous solid dispersion of 5-fluoro-1-(4-fluoro-3-(4-(pyrimidin-2-yl)piperazine-1-carbonyl)benzyl)quinazoline-2,4(1H,3H)-dione:HP-55 (1:3) in Bergle male dogs was 51.9%.

In summary, Examples 11~13 showed the oral absorption rates of the amorphous solid dispersion of 5-fluoro-1-(4-fluoro-3-(4-(pyrimidin-2-yl)piperazine-1-carbonyl)benzyl)quinazoline-2,4(1H,3H)-dione:HP-55 (1:3) in mice, rats, and dogs were very high, which can be used for administration to human.

Example 14

Production of the Amorphous Solid Dispersion of 5-fluoro-1-(4-fluoro-3-(4-(pyrimidin-2-yl)piperazine-1-carbonyl)benzyl)quinazoline-2,4(1H,3H)-dione:HP-55 (1:3)

THF and methanol (7:3, 8729 mL:3740 mL) (API &HP-55:solvent=1:25, w/v) were added to a glass container and stirred evenly. Then 5-fluoro-1-(4-fluoro-3-(4-(pyrimidin-2-yl)piperazine-1-carbonyl)benzyl)quinazoline-2,4(1H,3H)-dione (128.6 g) was added, and the mixture had been stirred continuously until a clear solution is formed. HP-55 (371.4 g) was added to the solution, following stirring to get a transparent or near transparent solution. The above solution was spray dried by using Niro SD-Micro spray dryer with seated parameters (Inlet temperature of 85° C., Outlet temperature 45° C.). After spray is completed, the solid dispersion was dried on line for about 15 min, and then put on the stainless steel tray and dried for about 96 h under vacuum (−0.09 to −0.1 MPa) at 45° C.

Example 15

Production of the Amorphous Solid Dispersion Capsules of 5-fluoro-1-(4-fluoro-3-(4-(pyrimidin-2-yl)piperazine-1-carbonyl)benzyl)quinazoline-2,4(1H,3H)-dione 1 mg Capsule and 10 mg capsule of the amorphous solid dispersion of 5-fluoro-1-(4-fluoro-3-(4-(pyrimidin-2-yl)piperazine-1-carbonyl)benzyl)quinazoline-2,4(1H,3H)-dione were manufactured by Xcelodose 600. Capsule HG, Size 0, a Swedish Orange Opaque cap, 22.820/a Swedish Orange Opaque body 22.820.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A solid dispersion powder, consisting of 25 wt % of 5-fluoro-1-(4-fluoro-3-(4-(pyrimidin-2-yl)piperazine-1-carbonyl)benzyl)quinazoline-2,4(1H,3H)-dione and 75 wt % of a polymer which is hydroxypropyl methyl cellulose phthalate, wherein the 5-fluoro-1-(4-fluoro-3-(4-(pyrimidin-2-yl)piperazine-1-carbonyl)benzyl)quinazoline-2,4(1H,3H)-dione is amorphous and consists of less than 10 wt % of crystalline 5-fluoro-1-(4-fluoro-3-(4-(pyrimidin-2-yl)piperazine-1-carbonyl)benzyl)quinazoline-2,4(1H,3H)-dione.

2. The solid dispersion powder according to claim 1, wherein the powder is substantially free of crystalline 5-fluoro-1-(4-fluoro-3-(4-(pyrimidin-2-yl)piperazine-1-carbonyl)benzyl)quinazoline-2,4(1H,3H)-dione.

3. The solid dispersion powder according to claim 1, wherein the solid dispersion powder is obtained by spray drying.

4. A pharmaceutical composition, consisting of a solid dispersion powder and a pharmaceutically acceptable carrier, wherein the solid dispersion powder consists of (a) 25 wt % of 5-fluoro-1-(4-fluoro-3-(4-(pyrimidin-2-yl)piperazine-1-carbonyl)benzyl)quinazoline-2,4(1H,3H)-dione, wherein the 5-fluoro-1-(4-fluoro-3-(4-(pyrimidin-2-yl)piperazine-1-carbonyl)benzyl)quinazoline-2,4(1H,3H)-dione is amorphous and consists of less than 10 wt % of crystalline 5-fluoro-1-(4-fluoro-3-(4-(pyrimidin-2-yl)piperazine-1-carbonyl)benzyl)quinazoline-2,4(1H,3H)-dione, and (b) 75 wt % of a polymer which is hydroxypropyl methyl cellulose phthalate.

5. The pharmaceutical composition according to claim 4, wherein the solid dispersion powder is substantially free of crystalline 5-fluoro-1-(4-fluoro-3-(4-(pyrimidin-2-yl)piperazine-1-carbonyl)benzyl)quinazoline-2,4(1H,3H)-dione.

6. The pharmaceutical composition according to claim 4, wherein the solid dispersion powder is obtained by spray drying.

7. A pharmaceutical composition consisting of a solid dispersion powder, and at least one anti-cancer drug, wherein the solid dispersion powder consists of (a) 25 wt % of 5-fluoro-1-(4-fluoro-3-(4-(pyrimidin-2-yl)piperazine-1-carbonyl)benzyl)quinazoline-2,4(1H,3H)-dione, wherein the 5-fluoro-1-(4-fluoro-3-(4-(pyrimidin-2-yl)piperazine-1-carbonyl)benzyl)quinazoline-2,4(1H,3H)-dione is amorphous and consists of less than 10 wt % of crystalline 5-fluoro-1-(4-fluoro-3-(4-(pyrimidin-2-yl)piperazine-1-carbonyl)benzyl)quinazoline-2,4(1H,3H)-dione and (b) 75 wt % of a polymer which is hydroxypropyl methyl cellulose phthalate, and wherein the at least one anti-cancer drug is selected from the group consisting of busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, elliptinium, etoposide, 5-azacytidine, gemcitabine, 5-fluorouracil, methotrexate, 5-fluoro-2'-deoxy-uridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, campath, Panitumumab, Ofatumumab, Avastin, trastuzumab, rituximab, imatinib, gefitinib, erlotinib, lapatinib, sorafenib, sunitinib, nilotinib, dasatinib, pazopanib, temsirolimus, everolimus, vorinostat, romidepsin, tamoxifen, letrozole, fulvestrant, mitoguazone, octreotide, retinoic acid, arsenic trioxide, zoledronic acid, bortezomib, thalidomide, lenalidomide, and pharmaceutically acceptable salts thereof.

* * * * *